United States Patent
Feng et al.

(10) Patent No.: US 10,160,720 B1
(45) Date of Patent: Dec. 25, 2018

(54) AZOBENZENE-BASED PHOTOTHERMAL ENERGY STORAGE MOLECULE, METHOD FOR PREPARING THE SAME AND USE THEREOF

(71) Applicant: TIANJIN UNIVERSITY, Tianjin (CN)

(72) Inventors: Wei Feng, Tianjin (CN); Fei Zhai, Tianjin (CN); Yiyu Feng, Tianjin (CN); Weixiang Yang, Tianjin (CN); Liqi Dong, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 16/123,405

(22) Filed: Sep. 6, 2018

(30) Foreign Application Priority Data

Apr. 13, 2018 (CN) .......................... 2018 1 0329826

(51) Int. Cl.
C07C 245/08 (2006.01)
F24S 60/20 (2018.01)

(52) U.S. Cl.
CPC ............ *C07C 245/08* (2013.01); *F24S 60/20* (2018.05)

(58) Field of Classification Search
None
See application file for complete search history.

(56) References Cited

U.S. PATENT DOCUMENTS 9,345,781 B2 * 5/2016 El-Sayed ......... A61K 47/48192

* cited by examiner

*Primary Examiner* — Kamal A Saeed
(74) *Attorney, Agent, or Firm* — RatnerPrestia (57) ABSTRACT

Provided is an azobenzene-based photothermal energy storage molecule represented by Formula I which contains two types of azobenzene unit: two biscarboxyl azobenzene units and one monoamino azobenzene unit. By utilizing the energy difference between the two configurations of the azobenzene units, energy is stored during the transition from trans to cis, and in reverse, energy is released. The carboxyl and amino groups on different azobenzene units can form strong intermolecular and intramolecular hydrogen bonds, which leads to a great improvement in energy density and reversion half-life compared with the traditional azobenzene materials in which a single type of an azobenzene unit is grafted. Moreover, the release of thermal energy can be controlled by light and heating, which is beneficial to fully utilize the solar energy for photothermal energy conversion and storage, and used as a solar thermal fuel to the field of heating technology and new generation of light-driven spacecrafts.

10 Claims, 2 Drawing Sheets

Formula I

AZOBENZENE-BASED PHOTOTHERMAL ENERGY STORAGE MOLECULE, METHOD FOR PREPARING THE SAME AND USE THEREOF

CROSS REFERENCE TO RELATED APPLICATIONS

This application claims the priority of Chinese Patent Application No. 201810329826.0, filed on Apr. 13, 2018, and the disclosure of which is hereby incorporated by reference.

FIELD

The present invention relates to the technical field of photothermal energy storage, and in particular to an azobenzene-based photothermal energy storage molecule and a method for preparing the same and use thereof.

BACKGROUND

Meeting the growing global energy demand in a sustainable way can be regarded as the most significant scientific challenge in our era. In response to this challenge, significant technological innovations are required, which in turn require advances in basic science, especially studies on basic processes such as solar energy capture, conversion and storage. Researchers have made considerable efforts to develop photocatalytic decomposition of $H_2O$ into $H_2$ and $O_2$, conversion of $CO_2$ and $H_2O$ to $CH_3OH$ and $O_2$, and similar conversion for energy absorption. Such researches have received extensive attention in the chemical and material sciences. Another solar energy storage strategy which has been relatively unexplored to date is that high-energy metastable compounds are generated by using photochemistry, which, at a later time, are capable of releasing large amounts of heat through their thermal isomerization. Such a process of a photoisomerization reaction followed by reversion of isomerization to release heat can be repeated multiple times, which represents a closed cycle of storing the solar energy by using high-energy chemical bonds. This process offers unique attributes that make this cycle a useful hybrid solution for solar energy capture, storage and utilization. This process is one that photosensitive molecules are used to both convert and store solar energy using the same material. These molecules convert the solar energy into tight or rearranged chemical bonds and thereby have an energy storage space, i.e. the energy difference between the ground state and the metastable state. A parent photoisomer is converted to a high-energy metastable photoisomer by irradiation of light. The photoisomer is then converted to the original parent compound by exposure to a catalyst or by heating. During the reversion of conversion, the photoisomer releases the stored energy in a form of heat. These materials are used for solar energy capture and thus are referred to as solar thermal fuels, which operate in a closed cycle having a high energy density without degradation or divergence in an ideal state and can conveniently distribute the stored solar energy according to "heat demand".

An azobenzene is a photoresponsive material having both cis and trans configurations, which meets the requirements of this method. Under the irradiation of ultraviolet light with a specific wavelength, the azobenzene in a trans configuration is converted into a cis configuration; and thereafter, under light or heat conditions, the cis configuration can be reverted to the trans configuration. There is an energy difference between the two configurations, in which transition from a trans configuration to a cis configuration can store energy, and in reverse, heat can be released. As a photothermal energy storage material, there are several factors that need to be optimized, including the energy storage density, solar spectrum matching (the ability of a molecule to absorb large bands of the solar spectrum), quantum yield of the light conversion, half-life of high-energy isomers, and height of an energy barrier to revert the conversion, etc. However, simultaneous optimization of these factors in a single molecule system is very challenging. The azobenzene has a good cycle performance and is therefore widely used in various optical switches; however, its application in photothermal storage is limited by its low energy density.

SUMMARY

In view of this, the technical problem to be solved by an aspect of the present invention is to provide an azobenzene-based photothermal energy storage molecule and a preparation method and use thereof, and the prepared azobenzene-based photothermal energy storage molecule has a high energy density and a short half-life.

An aspect of the present invention provides an azobenzene-based photothermal energy storage molecule having the structure represented by Formula I:

Formula I

The azobenzene-based photothermal energy storage molecule contains per molecule three azobenzene units which are linked to the same benzene ring via covalent bonds, two of which are biscarboxyl azobenzene units and one of which is a monoamino azobenzene unit. The molecular structure of such a molecule is macroscopically symmetrical, which allows its electron cloud to have a harmonic enhancement effect on photon transmission, and leads to a great improvement in single molecule energy value and reversion half-life compared with the conventional azobenzene materials.

The experimental results show that, for the above azobenzene-based photothermal energy storage molecule, the three azobenzene branches on the molecule can realize isomerization from trans to cis under the irradiation of light at a wavelength of 300~480 nm. Heat can be released under the irradiation of light at a wavelength of 520~620 nm, with an energy density up to 47~63 Wh/kg.

Under the irradiation of light at a wavelength of 520~620 nm, when the molecule is heated to 56~82° C., heat can be quickly released for 1 min~10 min; and at a low temperature, such as −5~10° C., heat can be slowly released.

An aspect of the present invention further provides a method for preparing the above azobenzene-based photothermal energy storage molecule, comprising the steps of:

subjecting trimethyl 1,3,5-benzenetricarboxylate to a hydrolysis reaction to obtain an intermediate represented by Formula II;

activating the intermediate represented by Formula II with oxalyl chloride, and then reacting with Disperse Orange 3 to obtain an intermediate represented by Formula III;

subjecting the intermediate represented by Formula III to a hydrolysis reaction to obtain an intermediate represented by Formula IV;

activating the intermediate represented by Formula IV with oxalyl chloride, and then reacting with biscarboxyl azobenzene to obtain an intermediate represented by Formula V;

reacting the intermediate represented by Formula V with $Na_2S$ to obtain the azobenzene-based photothermal energy storage molecule represented by Formula I;

Formula II

Formula III

Formula IV

Formula V

Formula I

A reaction scheme of the above preparation method is as follows:

(1)

(2)

(3)

(4)

(5)

The subjecting trimethyl 1,3,5-benzenetricarboxylate to a hydrolysis reaction is subjecting one molecule of an ester group to a hydrolysis reaction, and the conditions of the hydrolysis reaction in an aspect of the present invention are not particularly limited, and may be conditions for an ester hydrolysis reaction well-known to those skilled in the art. This step is preferably and specifically:

subjecting trimethyl 1,3,5-benzenetricarboxylate to a hydrolysis reaction under an alkaline condition, followed by acidification to obtain an intermediate represented by Formula II.

The alkaline condition is provided by an alkaline compound, such as NaOH, KOH and other alkaline compounds, and the molar ratio of the alkaline compound to the trimethyl 1,3,5-benzenetricarboxylate is preferably (1~1.2): 1.

The intermediate represented by Formula II is reacted with oxalyl chloride to be activated, and then reacted with Disperse Orange 3 to obtain an intermediate represented by Formula III.

The subjecting the intermediate represented by Formula III to a hydrolysis reaction is subjecting two molecules of an ester group to a hydrolysis reaction, and the conditions of the hydrolysis reaction in an aspect of the present invention are not particularly limited, and may be conditions for an ester hydrolysis reaction well-known to those skilled in the art. This step is preferably and specifically:

subjecting the intermediate represented by Formula III to a hydrolysis reaction under an alkaline condition, followed by acidification to obtain an intermediate represented by Formula IV.

The alkaline condition is provided by an alkaline compound, such as NaOH, KOH and other alkaline compounds, and the molar ratio of the alkaline compound to the intermediate represented by Formula III is preferably (2~2.4):1.

The intermediate represented by Formula IV is reacted with oxalyl chloride to be activated, and then reacted with biscarboxyl azobenzene to obtain an intermediate represented by Formula V, which is then reacted with $Na_2S$ to obtain an azobenzene-based photothermal energy storage molecule represented by Formula I.

In some specific embodiments of an aspect of the present invention, taking trimethyl 1,3,5-benzenetricarboxylate in a feeding amount of 3.6~4.0 g as an example, the preparation method is specifically by the following steps:

(1) Preparation of an Intermediate Represented by Formula II 3.6~4.0 g of trimethyl 1,3,5-benzenetricarboxylate and 0.5~0.8 g of NaOH are dissolved in 110 ml of methanol, and slowly warmed to a reflux temperature with stirring for 8~14 hours, and then the solvent is removed by rotary evaporation. The product is dissolved with dichloromethane and then extracted with a saturated sodium bicarbonate solution. The extracted aqueous phase is washed twice with dichloromethane and then adjusted to pH=1~1.5 with HCl, and a precipitate is produced. The precipitate is washed with water until neutral and the product is dried in a vacuum oven.

(2) Preparation of an Intermediate Represented by Formula III 2.5~3 g of the intermediate represented by Formula II is dissolved in 80~100 ml of acetonitrile, and 1.5~1.8 ml of oxalyl chloride (about 1.2 equivalents) and 30~50 μL of DMF are added thereto under nitrogen protection, to perform a reaction at normal temperature for 3~5 hours. 3.8~4.2 ml of triethylamine and 2.7~2.9 g of Disperse Orange 3 are then added to the system, which is reacted in an ice bath for 10 hours. The product is poured into water to generate a precipitate. The precipitate is washed successively with dilute hydrochloric acid, aqueous phase sodium bicarbonate and water, respectively. The obtained precipitate is dried in a vacuum oven at 60° C.

(3) Preparation of an Intermediate Represented by Formula IV

20~25 mmol of the intermediate represented by Formula III is dissolved in a mixed solution of 120~160 ml of THF and 30~60 ml of water. 2.4 equivalents (30~60 mmol) of NaOH is dissolved in 30~50 ml of water, and the resulting solution is added dropwise to the above mixed solution, to perform a reaction at reflux for 8~12 hours. THF in the solution is removed by rotary evaporation, and the residue is dissolved in water. The resultant is adjusted to pH=1.8~2.2 with hydrochloric acid, and a precipitate is generated. The precipitate is washed with water until neutral and dried in a vacuum oven at 60° C.

(4) Preparation of an Intermediate Represented by Formula V 3.6~4.0 g (7~10 mmol) of the intermediate represented by Formula IV is dissolved in 80~120 ml of dichloromethane, and 1.2~1.4 ml of oxalyl chloride and 38~40 μL of DMF are added thereto under nitrogen protection, to perform a reaction at normal temperature for 3.5~4.2 hours. Then, 4.18 ml of triethylamine (30 mmol) and 5.13 g of biscarboxyl azobenzene are added to the system, which is reacted in an ice bath for 40 hours. The solvent is removed from the product by rotary evaporation, and then the product is washed three times with dichloromethane/diethyl ether (volume ratio 1:1) to obtain a crude product. The crude product is dissolved in a large amount of distilled water, and adjusted to pH=1.8~2.0 in an ice bath to generate a precipitate. The precipitate is dried in a vacuum oven at 60° C.

(5) Preparation of an Azobenzene-Based Photothermal Energy Storage Molecule Represented by Formula I The intermediate represented by Formula V (4.5~4.8 g, 3~5 mmol) is dissolved in a mixed solution of 80~100 ml of water and 20~30 ml of DMF. NaS.9H$_2$O (2.2~2.6 g, 9~11 mmol) is then dissolved in 80~100 ml of water, and added dropwise to the above system and refluxed for 30~36 hours. When the reaction is completed, the solvent is removed by rotary evaporation. The precipitate is re-dissolved in a large amount of water and adjusted to pH=8.0~8.5 with an ammonium salt, and the aqueous phase is extracted with dichloromethane. The dichloromethane is spin-dried, and the obtained solid is maintained in a vacuum oven until constant weight to obtain an azobenzene-based photothermal energy storage molecule represented by Formula I, which is referred to a three-branched azobenzene below.

An aspect of the present invention provides use of the above azobenzene-based photothermal energy storage molecule or the azobenzene-based photothermal energy storage molecule prepared by the above preparation method as a solar thermal fuel.

The solar thermal fuel can be applied in the field of heating technology and light-driven spacecrafts.

Compared with the prior art, an aspect of the present invention provides an azobenzene-based photothermal energy storage molecule having the structure represented by Formula I. Such a molecule contains two types of azobenzene units per molecule, with one type being two biscarboxyl azobenzene units and another being one monoamino azobenzene unit. By utilizing the energy difference between the two configurations of the azobenzene units, energy can be stored when transition from trans to cis, and in reverse, energy can be released. The special molecular structure thereof is macroscopically symmetrical, and the carboxyl and amino groups on different azobenzene units can form strong intermolecular and intramolecular hydrogen bonds, which leads to a great improvement in energy density value and reversion half-life compared with the traditional azobenzene materials in which a single type of an azobenzene unit is grafted. Moreover, the azobenzene-based photothermal energy storage molecule can realize controlled release of thermal energy by light irradiation and heating, which is beneficial to fully utilize the solar energy for photothermal energy conversion and storage, and thus is applied as a solar thermal fuel to the field of heating technology and space light-controlled driving for a new generation of spacecrafts.

DETAILED DESCRIPTION OF EMBODIMENTS

Hereinafter, the azobenzene-based photothermal energy storage molecule and preparation method and use thereof of aspects of the present invention will be described in detail in combination with examples in order to further illustrate aspects of the present invention.

Example 1

Synthesis of Product 1

3.7515 g of trimethyl 1,3,5-benzenetricarboxylate and 0.5798 g of NaOH were dissolved in 110 ml of methanol, and slowly warmed to a reflux temperature with stirring for 12 hours, and then the solvent was removed by rotary evaporation. The product was dissolved with dichloromethane and then extracted with a saturated sodium bicarbonate solution. The extracted aqueous phase was washed twice with dichloromethane and then adjusted to pH=1 with HCl, and a precipitate was produced. The precipitate was washed with water until neutral and the product was dried in a vacuum oven to obtain product 1.

2.856 g of product 1 was dissolved in 100 ml of acetonitrile, and 1.78 ml of oxalyl chloride (1.2 equivalents) and 50 μL of DMF were added thereto under nitrogen protection, to perform a reaction at normal temperature for 4 hours. 4.18 ml of triethylamine and 2.9 g of Disperse Orange 3 were then added to the system, which was reacted in an ice bath for 10 hours. The product was poured into water to generate a precipitate. The precipitate was washed successively with dilute hydrochloric acid, aqueous phase sodium bicarbonate and water, respectively. The obtained precipitate was dried in a vacuum oven at 60° C. to obtain product 2.

22 mmol of product 2 was dissolved in a mixed solution of 150 ml of THF and 50 ml of water. 2.4 equivalents of NaOH was dissolved in 40 ml of water, and the resulting solution was added dropwise to the above mixed solution, to perform a reaction at reflux for 10 hours. THF in the solution was removed by rotary evaporation, and the residue was dissolved in water. The resultant was adjusted to pH=2 with hydrochloric acid, and a precipitate was generated. The precipitate was washed with water until neutral and dried in a vacuum oven at 60° C. to obtain product 3.

3.9 g (9 mmol) of product 3 was dissolved in 100 ml of dichloromethane, and 1.34 ml of oxalyl chloride and 40 μL of DMF were added thereto under nitrogen protection, to perform a reaction at normal temperature for 4 hours. Then, 4.18 ml of triethylamine (30 mmol) and 5.13 g of biscarboxyl azobenzene were added to the system, which was reacted in an ice bath for 40 hours. The solvent was removed from the product by rotary evaporation, and then the product was washed three times with dichloromethane/diethyl ether (volume ratio 1:1) to obtain a crude product. The crude product was dissolved in a large amount of distilled water, and adjusted to pH=2 in an ice bath to generate a precipitate. The precipitate was dried in a vacuum oven at 60° C. to obtain product 4.

The product 4 (4.76 g, 5 mmol) was dissolved in a mixed solution of 100 ml of water and 30 ml of DMF. NaS.9H$_2$O (2.4 g, 10 mmol) was then dissolved in 100 ml of water, and added dropwise to the above system and refluxed for 36 hours. When the reaction was completed, the solvent was removed by rotary evaporation. The precipitate was re-dissolved in a large amount of water and adjusted to pH=8 with an ammonium salt, and the aqueous phase was extracted with dichloromethane. The dichloromethane was spin-dried, and the obtained solid was maintained in a vacuum oven until constant weight to obtain a three-branched azobenzene. Yield: 65%, purity: 98%.

The three-branched azobenzene was detected to have an energy density of 63 Wh/kg.

Figure 1:
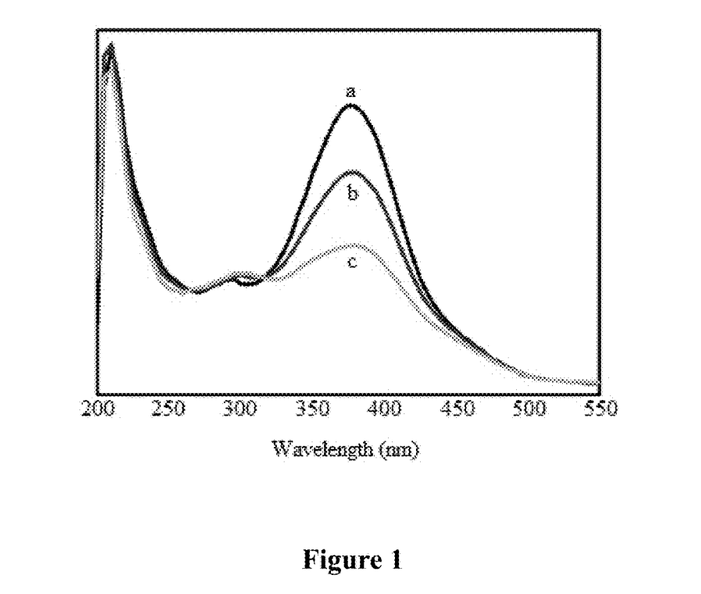
FIG. 1 is a diagram showing reversion of isomerization by ultraviolet absorption spectroscopy for an azobenzene-based photothermal energy storage material after light irradiation at 500~600 nm.

The prepared azobenzene-based photothermal energy storage material was irradiated with light at 500~600 nm, and the diagram of reversion of isomerization by ultraviolet absorption spectroscopy thereof is shown in FIG. 1, in which curve a is a curve of light irradiation for 10 min, curve b is a curve of light irradiation for 5 min, and curve c is a curve of light irradiation for 1 min.

As can be seen from FIG. 1, the cis three-branched azobenzene material undergoes a change in ultraviolet absorption due to reversion of isomerization from cis to trans over time under the irradiation of light at a wavelength of 500~600 nm. It can be seen that as the light irradiation time increases, the trans characteristic absorption peak is significantly enhanced, representing the reversion of isomerization from cis to trans.

The curves from c to a are of structure reversion after 1 min to 10 min, and the trend of change is that the trans characteristic absorption peak is significantly enhanced, representing the reversion from cis to trans, which indicates that the above cis three-branched azobenzene material has a short half-life of 10 min.

Figure 2:
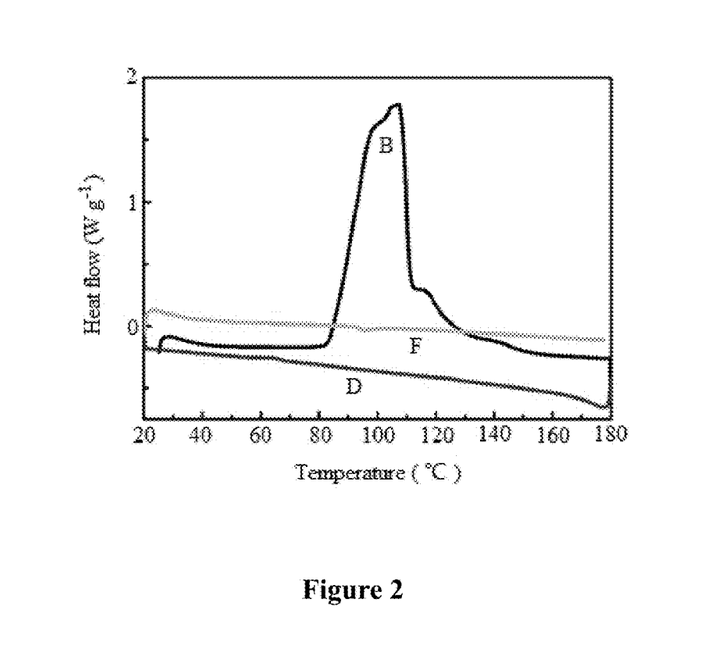
FIG. 2 is a DSC diagram of an azobenzene-based photothermal energy storage material.

The three-branched azobenzene was detected for its exotherm using differential scanning calorimetry, and the DSC diagram is shown in FIG. 2.

The exothermic curves of the three-branched azobenzene by a differential scanning calorimeter (DSC) can be seen from FIG. 2, in which a distinct exothermic peak is observed in B which is the first heating curve, while no exothermic peak is observed in both D which is the first cooling curve and F which is the second heating curve.

Figure 3:
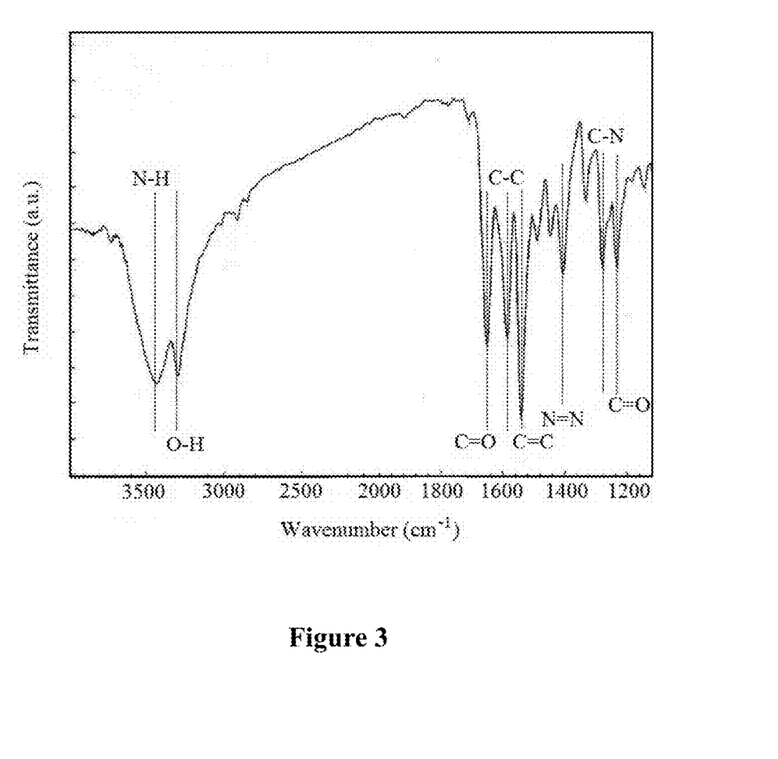
FIG. 3 is an infrared spectrum of the azobenzene-based photothermal energy storage material prepared in Example 1.

The three-branched azobenzene was detected for its structure using infrared spectroscopy, and the results are shown in FIG. 3.

Example 2

Synthesis of Product 1

3.9231 g of trimethyl 1,3,5-benzenetricarboxylate and 0.6453 g of NaOH were dissolved in 110 ml of methanol, and slowly warmed to a reflux temperature with stirring for 13 hours, and then the solvent was removed by rotary evaporation. The product was dissolved with dichloromethane and then extracted with a saturated sodium bicarbonate solution. The extracted aqueous phase was washed twice with dichloromethane and then adjusted to pH=1.2 with HCl, and a precipitate was produced. The precipitate was washed with water until neutral and the product was dried in a vacuum oven to obtain product 1.

2.648 g of product 1 was dissolved in 90 ml of acetonitrile, and 1.62 ml of oxalyl chloride (1.2 equivalents) and 42 μL of DMF were added thereto under nitrogen protection, to perform a reaction at normal temperature for 3.4 hours. 3.85 ml of triethylamine and 2.8 g of Disperse Orange 3 were then added to the system, which was reacted in an ice bath for 10 hours. The product was poured into water to generate a precipitate. The precipitate was washed successively with dilute hydrochloric acid, aqueous phase sodium bicarbonate and water, respectively. The obtained precipitate was dried in a vacuum oven at 60° C. to obtain product 2.

21 mmol of product 2 was dissolved in a mixed solution of 135 ml of THF and 45 ml of water. 2.4 equivalents of NaOH was dissolved in 38 ml of water, and the resulting solution was added dropwise to the above mixed solution, to perform a reaction at reflux for 9 hours. THF in the solution was removed by rotary evaporation, and the residue was dissolved in water. The resultant was adjusted to pH=1.8 with hydrochloric acid, and a precipitate was generated. The precipitate was washed with water until neutral and dried in a vacuum oven at 60° C. to obtain product 3.

3.8 g of product 3 was dissolved in 90 ml of dichloromethane, and 1.25 ml of oxalyl chloride and 38 μL of DMF were added thereto under nitrogen protection, to perform a reaction at normal temperature for 3.8 hours. Then, 4.18 ml of triethylamine (30 mmol) and 5.13 g of biscarboxyl azobenzene were added to the system, which was reacted in an ice bath for 40 hours. The solvent was removed from the product by rotary evaporation, and then the product was washed three times with dichloromethane/diethyl ether (volume ratio 1:1) to obtain a crude product. The crude product was dissolved in a large amount of distilled water, and adjusted to pH=1.8 in an ice bath to generate a precipitate. The precipitate was dried in a vacuum oven at 60° C. to obtain product 4.

4.55 g of product 4 was dissolved in a mixed solution of 90 ml of water and 25 ml of DMF. 2.5 g of NaS.9H$_2$O was then dissolved in 90 ml of water, and added dropwise to the above system and refluxed for 33 hours. When the reaction was completed, the solvent was removed by rotary evaporation. The precipitate was re-dissolved in a large amount of water and adjusted to pH=8.2 with an ammonium salt, and the aqueous phase was extracted with dichloromethane. The dichloromethane was spin-dried, and the obtained solid was maintained in a vacuum oven until constant weight to obtain a three-branched azobenzene. Yield: 57%, purity: 86%.

The three-branched azobenzene was detected to have an energy density of 52 Wh/kg.

Example 3

Synthesis of Product 1

3.7768 g of trimethyl 1,3,5-benzenetricarboxylate and 0.7439 g of NaOH were dissolved in 110 ml of methanol, and slowly warmed to a reflux temperature with stirring for 11 hours, and then the solvent was removed by rotary evaporation. The product was dissolved with dichloromethane and then extracted with a saturated sodium bicarbonate solution. The extracted aqueous phase was washed twice with dichloromethane and then adjusted to pH=1.3 with HCl, and a precipitate was produced. The precipitate was washed with water until neutral and the product was dried in a vacuum oven to obtain product 1.

2.976 g of product 1 was dissolved in 96 ml of acetonitrile, and 1.78 ml of oxalyl chloride (1.2 equivalents) and 49 μL of DMF were added thereto under nitrogen protection, to perform a reaction at normal temperature for 4.5 hours. 4.15 ml of triethylamine and 2.86 g of Disperse Orange 3 were then added to the system, which was reacted in an ice bath for 10 hours. The product was poured into water to generate a precipitate. The precipitate was washed successively with dilute hydrochloric acid, aqueous phase sodium bicarbonate and water, respectively. The obtained precipitate was dried in a vacuum oven at 60° C. to obtain product 2.

23 mmol of product 2 was dissolved in a mixed solution of 144 ml of THF and 46 ml of water. 2.4 equivalents of NaOH was dissolved in 43 ml of water, and the resulting solution was added dropwise to the above mixed solution, to perform a reaction at reflux for 8.8 hours. THF in the solution was removed by rotary evaporation, and the residue was dissolved in water. The resultant was adjusted to pH=2.1 with hydrochloric acid, and a precipitate was generated. The precipitate was washed with water until neutral and dried in a vacuum oven at 60° C. to obtain product 3.

3.93 g of product 3 was dissolved in 113 ml of dichloromethane, and 1.33 ml of oxalyl chloride and 39 μL of DMF were added thereto under nitrogen protection, to perform a reaction at normal temperature for 3.9 hours.

Then, 4.18 ml of triethylamine (30 mmol) and 5.13 g of biscarboxyl azobenzene were added to the system, which was reacted in an ice bath for 40 hours. The solvent was removed from the product by rotary evaporation, and then the product was washed three times with dichloromethane/ diethyl ether (volume ratio 1:1) to obtain a crude product. The crude product was dissolved in a large amount of distilled water, and adjusted to pH=1.9 in an ice bath to generate a precipitate. The precipitate was dried in a vacuum oven at 60° C. to obtain product 4.

4.67 g of product 4 was dissolved in a mixed solution of 94 ml of water and 26 ml of DMF. 2.3 g of NaS.9H$_2$O was then dissolved in 90 ml of water, and added dropwise to the above system and refluxed for 35 hours. When the reaction was completed, the solvent was removed by rotary evaporation. The precipitate was re-dissolved in a large amount of water and adjusted to pH=8.1 with an ammonium salt, and the aqueous phase was extracted with dichloromethane. The dichloromethane was spin-dried, and the obtained solid was maintained in a vacuum oven until constant weight to obtain a three-branched azobenzene. Yield: 72%, purity: 93%.

The three-branched azobenzene was detected to have an energy density of 48 Wh/kg.

As can be seen from the above examples, the azobenzene-based photothermal energy storage molecule prepared by an aspect of the present invention has a high energy density and a short half-life.

The foregoing description of the examples is provided merely to help understanding the method of an aspect of the present invention and the core idea thereof. It should be pointed out that those skilled in the art can also make several improvements and modifications without departing from the principle of aspects of the present invention, and these improvements and modifications also fall within the scope of protection of the claims of the aspects of the present invention.

The invention claimed is:

1. An azobenzene-based photothermal energy storage molecule having a structure represented by Formula I:

Formula I

2. A method for preparing the azobenzene-based photothermal energy storage molecule according to claim 1, comprising:
subjecting trimethyl 1,3,5-benzenetricarboxylate to a hydrolysis reaction to obtain an intermediate represented by Formula II;
activating the intermediate represented by Formula II with oxalyl chloride, and then reacting with Disperse Orange 3 to obtain an intermediate represented by Formula III;
subjecting the intermediate represented by Formula III to a hydrolysis reaction to obtain an intermediate represented by Formula IV;
activating the intermediate represented by Formula IV with oxalyl chloride, and then reacting with biscarboxyl azobenzene to obtain an intermediate represented by Formula V; and
reacting the intermediate represented by Formula V with Na$_2$S to obtain the azobenzene-based photothermal energy storage molecule represented by Formula I;

-continued

Formula IV

Formula V

-continued

Formula I

3. The method according to claim 2, wherein the subjecting trimethyl 1,3,5-benzenetricarboxylate to a hydrolysis reaction is:
subjecting trimethyl 1,3,5-benzenetricarboxylate to a hydrolysis reaction under an alkaline condition, followed by acidification.

4. The method according to claim 3, wherein the alkaline condition is provided by an alkaline compound, and the molar ratio of the alkaline compound to trimethyl 1,3,5-benzenetricarboxylate is (1~1.2): 1.

5. The method according to claim 2, wherein the subjecting the intermediate represented by Formula III to a hydrolysis reaction is:
subjecting the intermediate represented by Formula III to a hydrolysis reaction under an alkaline condition, followed by acidification.

6. The method according to claim 5, wherein the alkaline condition is provided by an alkaline compound, and the molar ratio of the alkaline compound to the intermediate represented by Formula III is (2~2.4): 1.

7. A method of using the azobenzene-based photothermal energy storage molecule according to claim 1 as a solar thermal fuel, comprising applying the azobenzene-based photothermal energy storage molecule to the solar thermal fuel.

8. The method according to claim 7, wherein the solar thermal fuel is used in the field of heating technology and light-driven spacecrafts.

9. A method of using the azobenzene-based photothermal energy storage molecule produced by the method according to claim 2 as a solar thermal fuel, comprising applying the azobenzene-based photothermal energy storage molecule to the solar thermal fuel.

10. The method according to claim 9, wherein the solar thermal fuel is used in the field of heating technology and light-driven spacecrafts.

* * * * *